(12) United States Patent
McAllister et al.

(10) Patent No.: US 7,166,464 B2
(45) Date of Patent: Jan. 23, 2007

(54) METHOD OF CULTURING CELLS TO PRODUCE A TISSUE SHEET

(75) Inventors: Todd N. McAllister, Novato, CA (US); Nicolas L'Heureux, Corte Madera, CA (US)

(73) Assignee: Cytograft Tissue Engineering, Inc., Novato, CA (US)

( * ) Notice: Subject to any disclaimer, the term of this patent is extended or adjusted under 35 U.S.C. 154(b) by 547 days.

(21) Appl. No.: 10/318,279

(22) Filed: Dec. 11, 2002

(65) Prior Publication Data

US 2003/0138945 A1 Jul. 24, 2003

Related U.S. Application Data

(60) Provisional application No. 60/355,283, filed on Feb. 7, 2002, provisional application No. 60/340,964, filed on Dec. 11, 2001.

(51) Int. Cl.
*C12N 5/00* (2006.01)
*C12N 5/06* (2006.01)
*C12N 5/08* (2006.01)
*C12N 15/63* (2006.01)
*C12N 15/85* (2006.01)
*A61F 2/00* (2006.01)

(52) U.S. Cl. .................. 435/395; 424/423; 435/1.1; 435/325; 435/455

(58) Field of Classification Search .............. None
See application file for complete search history.

(56) References Cited

U.S. PATENT DOCUMENTS

| | | | |
|---|---|---|---|
| 4,546,500 A | 10/1985 | Bell | |
| 4,963,489 A | 10/1990 | Naughton et al. | |
| 5,443,950 A | 8/1995 | Naughton et al. | |
| 5,618,718 A | 4/1997 | Auger et al. | |
| 5,628,786 A | 5/1997 | Banas et al. | |
| 5,785,964 A | 7/1998 | Naughton et al. | |
| 5,792,603 A | 8/1998 | Dunkelman et al. | |
| 5,863,531 A | 1/1999 | Naughton et al. | |
| 5,865,723 A | 2/1999 | Love | |
| 5,962,325 A * | 10/1999 | Naughton et al. | 435/395 |
| 6,010,573 A | 1/2000 | Bowlin et al. | |
| 6,077,217 A | 6/2000 | Love et al. | |
| 6,121,042 A | 9/2000 | Peterson et al. | |
| 6,127,448 A | 10/2000 | Domb et al. | |
| 6,140,127 A | 10/2000 | Sprague et al. | |
| 6,206,914 B1 | 3/2001 | Soykan et al. | |
| 6,455,311 B1 * | 9/2002 | Vacanti | 435/395 |
| 6,468,300 B1 | 10/2002 | Freidberg | |

OTHER PUBLICATIONS

L'Heureux, et al., "A completely biological tissue-engineered human blood vessel," *The FASEB Journal*, vol. 12, pp. 47-56, Jan. 1998.

Scott, N.A. et al. "Seeding of intracoronary stents with immortalized human microvascular endothelial cells." *American Heart Journal*. vol. 129, No. 5, pp. 860-866, 1995.

* cited by examiner

*Primary Examiner*—David M. Naff
(74) *Attorney, Agent, or Firm*—Fish & Richardson P.C.

(57) ABSTRACT

The disclosure provides methods and systems for tissue engineering including an apparatus and methods for the growth, maintenance, and use of robust tissue sheets using tissue manipulation devices. The tissue manipulation devices provide a method of anchoring the tissue sheets to the cell culture substrate to promote prolonged maturation and subsequent increased mechanical strength. The tissue manipulation devices also provide a technique to facilitate removal of the sheet from the culture container and subsequent production steps to assemble more complex three dimensional organs from the robust sheet. The tissue manipulation devices also facilitate automated handling of the sheets in the assembly processes. The disclosure provides methods and composition derived from robust human sheets to build tissue engineered blood vessels, heart valves, stents, and endarterectomy patches and the like. The use of these tissue manipulation devices facilitates the assembly of complex tissue engineered organs using the novel sheet-based tissue engineering approach.

24 Claims, 4 Drawing Sheets

METHOD OF CULTURING CELLS TO PRODUCE A TISSUE SHEET

CROSS-REFERENCE TO RELATED APPLICATIONS

This application claims the benefit of priority under 35 U.S.C. § 119 to provisional application Ser. Nos. 60/355,283, filed Feb. 7, 2002, and 60/340,964, filed Dec. 11, 2001, the disclosures of which are incorporated herein by reference. The present application is also related to International Application Serial No. PCT/US02/39789, filed Dec. 11, 2002, entitled, "TISSUE ENGINEERED CELLULAR SHEETS, METHODS OF MAKING AND USE THEREOF," the disclosure of which is incorporated herein.

TECHNICAL FIELD

This invention relates to tissue engineering, and more particularly it relates to an apparatus and methods for the growth, maintenance, and use of tissue sheets with a tissue manipulation device.

BACKGROUND

There are currently efforts to construct tissue grafts in vitro to overcome the many problems posed by currently used artificial extra-corporeal and implanted devices. Such tissue engineering techniques include the creation, design, and fabrication of biological prosthetic devices, in combination with synthetic or natural materials, for the augmentation or replacement of body tissues and organs. However, the use of synthetic materials often results in the release of products and by-products in vivo that induce inflammation, lead to the production of inflammatory mediators, and may induce autoimmune disorders. The use of natural materials such as bovine collagen and decellularized extracellular matrix material from xenogeneic and allogeneic sources pose a risk of passing on pathogens to a recipient, including, such pathogens obtained from both human materials (e.g., HIV and HBV) and non-human materials (e.g., prions associated with bovine materials, and the like). In short, the failure mechanism of most tissue-engineered organs is associated directly with the presence of synthetic materials, which trigger various foreign body responses. This is particularly true of tissue engineered vascular grafts that must operate in the most immune sensitive environment in the body.

Vascular disease is typically associated with a severe narrowing of coronary and/or peripheral arteries which compromise organ function by restricting the flow of blood to downstream organs. There are three treatment strategies to repair these diseased arteries. The simplest repair is a catheter-based therapy called angioplasty, where an inflatable balloon is introduced via catheter to the damaged area and then expanded, thus disrupting the atherosclerotic plaque. Although these procedures are relatively inexpensive and pose little threat to the patient, angioplasty is associated with very poor long-term patency rates. A more effective version of this treatment involves the placement of a plastic deformable metallic stent inside the artery. This stent, when expanded, helps to hold the artery open after the balloon is removed. The primary limitation associated with stenting is that the synthetic material (usually nickel based steel, stainless steel, or Nitenol) used for the stent initiates a chronic inflammatory response and triggers a migration of cells toward the lumen of the blood vessel. This process, called intimal hyperplasia, results in a second narrowing of the diseased artery (restenosis). The third treatment option is a surgically placed bypass graft, which re-routes blood flow around the blockage through a new conduit, ideally made from a vein or artery harvested from another site in the subject's own body. In large diameter vessels ($\geq 6$ mm inside diameter) these bypass conduits can also be made from synthetic materials such as ePTFE. In most cases, clinical treatment strategies try the relatively non-invasive catheter based angioplasty/stenting before advancing to bypass surgery.

Although bypass procedures are known to have the highest long-term efficacy, the cost and risk associated with such an invasive surgical procedure often dictates that stenting is attempted as the primary treatment method.

In an attempt to increase the efficacy of stenting, new-generation stents have been developed that are coated with drug/protein-impregnated polymers. As the polymer resorbs, the drug, which discourages local cell migration or proliferation (intimal hyperplasia), is eluted into the blood stream. These stents have demonstrated phenomenal success rates in mid-term clinical studies (0–2 years), but, their long-term efficacy after the protein coating is completely resorbed is in question. More recently, advances in cell biology and genetic modifications have given rise to another generation of stent technologies, called cell seeded or living stents. In this configuration, cells are seeded onto the struts of the stent and then implanted. Although few clinical studies have been published on this technology, three limitations exist. First, relatively few cells can be loaded onto the small struts of the stent. Second, when the stent is expanded, the struts slide relative to each other, thus scraping many of the cells from the stent. Third, the cell coating does not offer any sort of membrane to either reduce the inflammatory response to the foreign material or to provide a barrier to prevent cell migration through the stent to the lumen of the vessel.

SUMMARY

The invention provides a tissue culture method. The tissue culture method comprising culturing a population of adherent cells in a tissue culture container in the presence of at least one tissue manipulation device, under conditions that allow the formation of a tissue sheet comprised of living cells and extracellular matrix formed by the cells, whereby the tissue sheet is in contact with the at least one tissue manipulation device; and removing the tissue sheet from the culture container.

The invention also provides a system for manipulation of a tissue in vitro. The system comprises a culture container comprising at least one wall, a bottom, and an upper opening, each of the at least one wall and the bottom having an inner and outer surface thereby forming an inside and an outside, the at least one wall and bottom comprised of a biocompatible material; at least one tissue manipulation device comprising a first end and a second end and at least one wall, wherein the at least one tissue manipulation device is substantially elongated from the first end to the second end, the at least one tissue manipulation device in juxtaposition with the at least one wall and/or bottom of the culture container; growing a tissue comprising a population of adherent cells in the culture container in the presence of the at least one tissue manipulation device such that the population of adherent cells grow to form a tissue sheet in contact with at least one tissue manipulation device and wherein the cells contact the inside of at least one wall of the vessel; and removing the tissue from the vessel using the at least one tissue manipulation device.

The invention provides a genetically engineered living stent. The genetically engineered living stent is generated by a method comprising culturing a population of adherent cells in a culture container in the presence of at least one tissue manipulation device under conditions to allow the formation of a tissue sheet comprised of cells and extracellular matrix formed by the cells in contact with the at least one tissue manipulation device whereby the at least one tissue manipulation device anchors the tissue sheet in the culture container and wherein at least one cell of the population of cells is transfected with an exogenous polynucleotide such that the exogenous polynucleotide expresses a product. The tissue sheet is removed from the culture container and formed into a tubular structure thereby forming a genetically engineered living stent.

The invention also provides a method of forming a genetically engineered living stent. The method includes culturing a population of adherent cells in a culture container in the presence of at least one tissue manipulation device under conditions to allow the formation of a tissue sheet comprised of cells and extracellular matrix formed by the cells in contact with the at least one tissue manipulation device whereby the at least one tissue manipulation device anchors the tissue sheet in the culture container and wherein at least one cell of the population of cells is transfected with an exogenous polynucleotide such that the exogenous polynucleotide expresses a product. The method further includes removing the tissue sheet from the culture container and formed into a tubular structure thereby forming a genetically engineered living stent.

The invention further provides a genetically engineered tissue sheet prepared in vitro. The genetically engineered tissue sheet comprises a population of adherent cells wherein at least one cell of the population of cells is transfected with an exogenous polynucleotide such that the exogenous polynucleotide expresses a product and culturing the population of adherent cells in a culture container in the presence of at least one tissue manipulation device such that the population of adherent cells grow to form a tissue sheet in contact with the at least one tissue manipulation device whereby the tissue sheet is anchored within the culture container by the at least one tissue manipulation device.

Also provided by the invention is a method for manipulation of a genetically engineered tissue sheet prepared in vitro. The method comprises culturing a population of adherent cells in a culture container in the presence of at least one tissue manipulation device under conditions to allow the formation of a tissue sheet comprised of cells and extracellular matrix formed by the cells in contact with the at least one tissue manipulation device whereby the at least one tissue manipulation device anchors the tissue sheet in the culture container and wherein at least one cell of the population of cells is transfected with an exogenous polynucleotide such that the exogenous polynucleotide expresses a product; removing the tissue sheet from the culture container; and forming a desired tissue structure.

The invention provides a living stent generated by a method comprising culturing a population of adherent cells in a culture container in the presence of at least one tissue manipulation device under conditions to allow the formation of a tissue sheet comprised of cells and extracellular matrix formed by the cells in contact with the at least one tissue manipulation device whereby the at least one tissue manipulation device anchors the tissue sheet in the culture container; removing the tissue sheet from the culture container; and contacting a biocompatible tubular device with the tissue sheet to form one or more layers of the tissue sheet in contact with the tubular structure thereby forming a living stent.

The invention further provides a composition, comprising a biocompatible stent comprising a therapeutic agent and a tissue sheet cultured in vitro substantially enveloping the biocompatible stent, wherein the tissue sheet is derived from a population of adherent cells cultured in a culture container in the presence of at least one tissue manipulation device, wherein the population of adherent cells grow to form the tissue sheet whereby the tissue sheet is in contact with the at least one tissue manipulation device.

The invention also provides a composition, comprising a tissue sheet of cells formed into a tubular structure by rolling the tissue sheet upon itself one or more times. The tissue sheet is derived from a population of adherent cells cultured in a culture container in the presence of at least one tissue manipulation device, wherein the population of adherent cells grow to form the tissue sheet anchored by the at least one tissue manipulation device.

The invention yet further provides a living stent. The living stent is generated by a method comprising culturing a population of adherent cells in a culture container under conditions to allow the formation of a tissue sheet comprised of living cells and extracellular matrix formed by the cells; removing the tissue sheet from the culture container; and forming a tubular structure with the tissue sheet by wrapping the tissue sheet one or more times around a tubular structure which is mounted on a temporary support mandrel, thereby forming a living stent.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
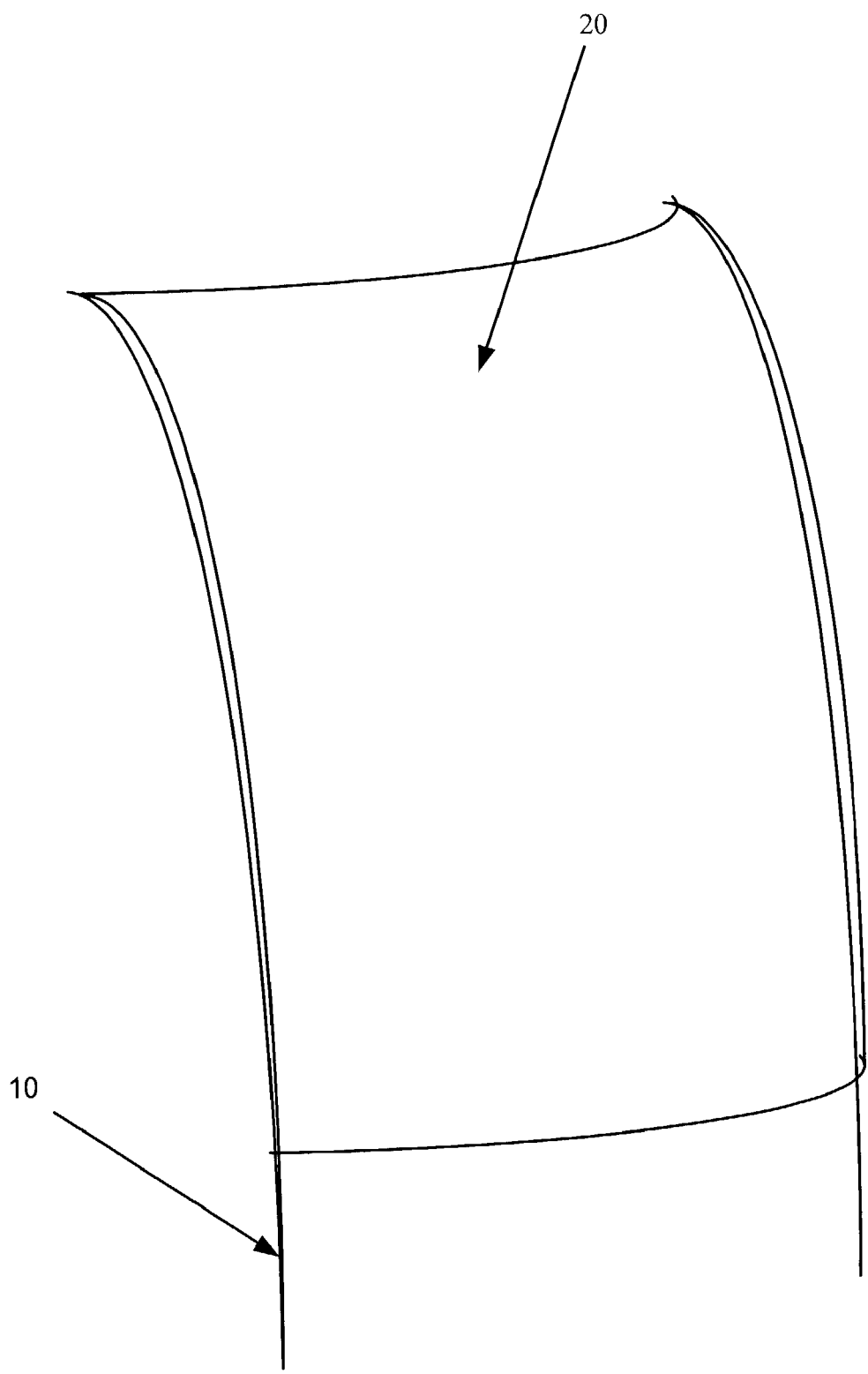
FIG. 1(a) is a schematic of a sample of tissue produced by sheet-based tissue engineering utilizing tissue control rods and methods according to the invention. The control rods (10) shown by arrows around the periphery of the tissue (20) are integrated into the tissue and allow the tissue to be held and easily manipulated. Typically, the sheet is approximately 10–200 microns thick.

As one beneficial aspect of the invention there is provided techniques to culture a subject's own cells into a robust tissue sheet. The invention provides compositions and methods to generate sheets of autologous and/or allogenic cells. These tissue sheets are robust and can be shaped or molded into a variety of organs, including blood vessels, heart valves, and the like. The cells in the sheet can be manipulated into a desired shape or structure prior to or during implantation to assist in the replacement of organs or to assist in the reconstruction and/or healing of an existing organ. Examples of tissues applicable to the techniques of the invention include vascular tissue, skin tissue, hepatic tissue, pancreatic tissue, neuronal tissue, urogenital tissue, gastrointestinal tissue, and musculoskeletal tissue. In addition, the cells in a robust tissue sheet can be genetically modified to express a diagnostic and/or a therapeutic product (e.g., polypeptides or polynucleotides) to generate a genetically engineered tissue graft.

One use of the techniques and compositions of the invention include, for example, the treatment of cardiovascular diseases and disorders. Current treatment strategies for blocked coronary arteries typically include different percutaneous interventions such as balloon angioplasty or stenting, or surgical bypass of the blocked artery. Balloon angioplasty is a catheter-based therapy where flow is restored through the blocked artery by inflating a balloon in the area afflicted with an atherosclerotic lesion. By breaking up the blockage, the vessel is reopened and blood flow is restored. In stenting, the balloon angioplasty is followed by the placement of an expandable metallic stent that holds the artery open after the balloon is removed. The advantage to these procedures is that they are catheter based, meaning they are less invasive and do not require open-heart surgery. In most cases, physicians will opt for one of the less invasive percutaneous (or catheter-based) approaches first. The downside to these procedures is that success rates beyond 6 months are as low as 50%. Most short-term failures are associated with thrombosis (the formation of blood clots on the inside of the vessel) due to the lack of a functional endothelial cell lining in the stent. Most long-term failures are caused by cell migration and in growth into the lumen of the vessel in a process called intimal hyperplasia.

More recently, however, advances in stenting technology have improved short- to mid-term patency rates. By adding controlled release drug coatings to the stents, cell in-growth that causes secondary closure (restenosis) of the vessel is diminished. Specifically, these stents are loaded with therapeutic agents such as Paclitaxel, rapamycin, heparin, or sirolimus to reduce local cell migration and proliferation. Early results with these drug eluting stents demonstrates lower restenosis within 6–9 months. However, the long-term efficacy with these drug-eluting stents is still questionable. As the drug degrades, it is quite possible that restenosis rates will increase. Another limitation to the stents is that the body recognizes the stent and polymer coating as a foreign body and initiates a foreign body inflammatory/immune response. This inflammatory/immune response contributes to long-term failures by triggering cell migration and subsequent intimal hyperplasia.

The invention provides methods and compositions that can be used to treat vascular diseases and disorders. In one aspect a cellular tissue sheet of the invention is rolled into a cylindrical or tubular structure to provide a very robust cylindrical tissue similar to a blood vessel or other organ comprising a lumen. Cell sheets of the invention comprised only of human fibroblasts can form cylindrical grafts with a demonstrated burst pressure greater than about 4000 mmHg (30 times physiological blood pressure). This cylindrical tissue sheet can be used as a stent, thus eliminating the need for a metallic stent. Moreover, it is possible to use the tissue sheet-based construct to perform a percutaneous bypass. In this embodiment, the construct is delivered via catheter by piercing through the wall of the healthy vessel near the proximal end of a diseased area of the vessel and bypassing the diseased area by re-entering the vessel on the distal end of the diseased area. A percutaneous bypass would not be possible with current technologies, since normal stents do not have a membrane that would allow blood to pass through without leaking.

Although described herein with particular reference to formation of vascular blood vessels, it should be understood that the tubular structures, generated by rolling a tissue sheet of the invention one or more times to generate a structure comprising a lumen surrounded by a sheet of cells, can be used to form lumens for passage of a variety of fluids, not just blood. Other fluids include, but are not limited to, urine, bile, and lymph.

A tissue is a multicellular organization of cells. Bodily tissue comprises a variety of cell types but typically have a population of cells of a defined lineage (sometimes referred to as parenchymal cells). In vitro tissues can be generated by culturing a population of cells under conditions that allow the cells to multiply and expand under tissue culture conditions. The cells present in a tissue culture may be the same or may comprise a combination of various cell types including, for example, stromal cells (e.g., fibroblasts or mesenchymal precursor cells) alone or in combination with various parenchymal cells of a bodily tissue (e.g., smooth muscle cells, endothelial cells, hepatocytes, keratinocytes, and the like). A tissue sheet comprises a population of cells having the same or different morphologies and/or lineages cultured in vitro under conditions whereby the cells grow and multiply.

The robust tissue sheets are special constructs. They are different from other standard cell cultures in many ways both structurally and physically. Structurally: 1) tissue sheet are comprised of multiple layer of cells, 2) the cells are embedded in a large amount of extracellular matrix proteins produced by the cells themselves, 3) the extracellular matrix proteins are "natural" in as much as they are not physically/chemically modified by extraction/isolation, procedures, 4) the extracellular matrix proteins are of various nature and offer a complex extracellular environment to the cells (similar to a physiological tissue environment), 5) the tridimensional organization of the extracellular protein matrix is also similar to the physiological tissue environment. Physically: 1) tissue sheet are thick (~50 to >200 µm) compared to a monolayer (~5 µm thick) and are easily visible to the naked eye, 2) they can be peeled off a culture substrate with regular tweezers, 3) they are peeled off the culture substrate as one single, intact sheet covering the entire culture surface and containing practically all the cells of the culture and the extracellular matrix proteins produced by the cells, 4) these sheets are robust enough that they can be easily manipulated with common surgical instruments, 5) these robust tissue sheets have shown a resistance to puncture exceeding a 800 gmf applied with a 8 mm spherical piston. To produce these tissue sheets, a cell population (homogenous or heterogeneous) is cultured in the presence of ascorbic acid, or one of its derivatives, as well as other commonly available culture media components, to promote extracellular matrix protein production. After an extended culture period, enough extracellular matrix protein is produced to make a coherent tissue sheet. These tissue sheets are now an integral part of the new field of tissue engineering, term sheet-based tissue engineering, and have been used to create skin, blood vessels, myocardial patches, vascular patches, heart valves, and soon, more complex organs. This novel technology allows for the first time the production of mechanically sound living tissues and organs, that can be made exclusively from these living tissue sheets without the need for any exogenous structural component such as synthetic scaffolds or animal/cadaver derived products. Furthermore, sheet-based tissue engineering opens the door to the production or tissues and organs made from a patients own cells, avoiding all rejection complications.

The sheet-based tissue engineering methods and compositions described herein utilize cells that are obtained and cultured in vitro into a robust sheet of cells. These sheets demonstrate puncture strength of about 50–100 grams force (gmf), typically about 100–300 gmf, more often about 300–800 gmf, but most often >800 gmf, a mechanical feature not found in any other tissue engineering or cell culture technology. For example, utilizing the techniques and methods described herein cells can be extracted from a biopsy (typically from the same subject into which the cell sheet will ultimately be implanted) and expanded in vitro. The cells can be genetically modified so that the genetically engineered cells over-express, for example, an anti-restenotic or anti-thrombogenic agent or an agent that increases the physical compliance of the cells to physiological stress. The unmodified or genetically modified cells are then grown into a robust tissue sheet which can then be used to form a tubular structure or which can be wrapped around a biocompatible stent to form a tissue-wrapped stent. The culturing of cells into a robust tissue sheet allows for a much higher density of cells to be delivered and, when the cells are genetically modified, to deliver a higher dosing range of, e.g., a therapeutic agent. The robust sheet of cells provides a fundamental difference/advantage over the current state of the art. For example, (1) the robust sheet allows for a much higher density of cells to be delivered and therefore higher dosing of therapeutic agents; (2) the robust sheet acts as a membrane such that blood does not leak through and cells cannot migrate through; (3) the robust sheet can be used to envelope a stent, thus delaying foreign body responses; and (4) the robust sheet can be endothelialized to provide an anti-thrombogenic surface on the lumen of a living stent or tissue-wrapped stent.

A tissue-wrapped stent (e.g., a robust sheet of cells wrapped about a stent) can also expand with the stent so that a significant portion of the cells are still living after stent placement. In one aspect, the sheet provides a coating for the synthetic stent such that the synthetic material of the biocompatible stent is "hidden" from the immune system. In addition, the coating of a biocompatible stent with the tissue sheet provides a significant barrier against cell migration/proliferation into the lumen of the stent thereby reducing the risk of intimal hyperplasia.

In another aspect, a tissue sheet of the invention is substantially decellularized to provide extracellular matrix materials provided by the population of cells. In some cases, it may be advantageous to decellularize or denature all or part of the tissue engineered construct. A decellularized sheet may have a reduced level of immunogenicity, and may provide a better matrix for endothelial seeding on the lumen, since the endothelial cells do not have to compete with the more proliferative or more robust cell types. Decellularizing or denaturing the sheet may also enhance the mechanical characteristics of the construct. The sheets, or the tissue within the construct, may be decellularized, denatured, or chemically modified using a variety of techniques. In the simplest embodiment, the sheet can be air-dried or lyopholized to kill the cells. Thermal shock, acoustic treatment, changes in pH, osmotic shock, mechanical disruption, or addition of toxins can also induce cell death or apoptosis. Similarly, the sheet can be crosslinked or fixed using agents such as paraformaldehyde. Other treatments to decellularize or denature the tissue are possible using radiation, detergents (SDS or triton ×100), enzymes (RNAase, DNAase), or solvents (alcohol, acetone, or chloroform). These techniques are only some of the examples of techniques to decellularize, denature or chemically modify all or part of the tissue and are not meant to limit the scope of the invention. For example, methods of decellularizing can utilize, for example, enzymes such as lipases combined with other enzymes and, optionally, detergents. See, for example, WO 9603093A and WO 9632905A, incorporated herein by reference. Treatment with hypotonic and/or hypertonic solutions, which have nonphysiological ionic strengths, can promote the decellularization process. These various decellularization solutions generally are suitable as treatment solutions. Proteases also can be used effectively to decellularize tissue. The decellularization can be performed in stages with some or all of the stages involving differential treatments. For example, a potent mixture of proteases, nucleases and phospholipases could be used in high concentrations to decellularize the tissue. The decellularized extracellular matrix may then have applied another tissue sheet or another decellularized sheet. For example, one can roll a living layer on top of a decellularized layer.

Sheet-based tissue engineering, and in particular a tubular sheet of cells or the tissue-wrapped stent described herein are different from prior tissue engineering art. Prior methods of generating tissue-engineered grafts had three fundamental aspects. First, prior tissue engineering grafts require the use of a three dimensional scaffold (such as a porous polymer or fabric) to provide mechanical support for the cells. Second, prior tissue culture techniques would not result in a robust tissue sheet that can be handled surgically. In fact, after a few weeks in culture, most cell culture techniques result in spontaneous detachment of the cells and loss of the culture. Third, prior tissue-engineering techniques relied heavily on allogeneic cell sources thereby inducing immune and/or inflammatory responses upon implantation into a subject, which promotes infiltration, and proliferation into the lumen of a vessel or stent, the primary long-term failure mode of other stenting technologies.

In one aspect, the invention provides a tissue-wrapped stent technology that addresses both the short-term and long-term failures as described above. As one beneficial aspect there is provided techniques to obtain cells from a subject, genetically modify the cells to over-express an anti-restenotic or anti-thrombogenic agent and then grow these modified cells into a robust tissue sheet. Examples of anti-restenotic or anti-thrombogenic agents include nitric oxide synthase, PGI2 (cyclooxygenase-1), tissue inhibitor of metalloproteinase-1 (or other MMP inhibitors), tissue plasminogen activator (or other thrombolytic agents), heparin and derivatives thereof, tissue factor pathway inhibitor (or other anti-inflammatory agents), and statins. The cells may also be modified to express anti-proliferation/activation products that can be triggered or suppressed (to control potential intimal hyperplasia) including, for example, retinoblastoma family of genes, E2F decoy, AP-1 decoy, cyclin-dependent kinase inhibitors, I kappa B alpha, and the like. During growth in culture the cells may be cultured with agents that promote cellular proliferation and growth. Such agents include a number of growth factors that can be selected based upon the tissue to be grown and the cell types present (e.g., keratinocyte growth factor (KGF); vascular endothelial cell growth factor (VEGF); platelet derived growth factor (PDGF); fibroblast growth factor (FGF); a transforming growth factor (TGF) alpha, beta, and the like; insulin; growth hormone; somatomedins; colony stimulating factors; erythropoietin; epidermal growth factor; hepatic erythropoietic factor (hepatopoietin); and liver-cell growth factor to name a few, others are known in the art). Serum, such as fetal bovine serum (FBS) or the like, can also provide some of these growth factors. In addition, agents such as ascorbic acid can be used to increase extracellular matrix production.

A tissue manipulation device (e.g., one or more such devices such as control rods) is used to secure a growing tissue sheet to a flask or other culture container and prevent spontaneous detachment. Moreover, the tissue manipulation device (e.g., control rods) allow for easier sheet handling while a tissue sheet is being wrapped around a stent or in the formation of a tubular structure. A tissue manipulation device may be added to a culture container before seeding with the cells. In some aspects of the invention a tissue manipulation device may be added after seeding a culture container with a population of cells (e.g., immediately after seeding the culture container or may passages or weeks after seeding the culture container). For example, tissue sheets typically begin to spontaneously detached after being in culture for a prolonged period of time, in one aspect of the invention, a tissue manipulation device is added to culture just prior to or during that stage of spontaneous detachment in order to further facilitate prolonged culture and development of a robust tissue sheet.

Figure 1B:
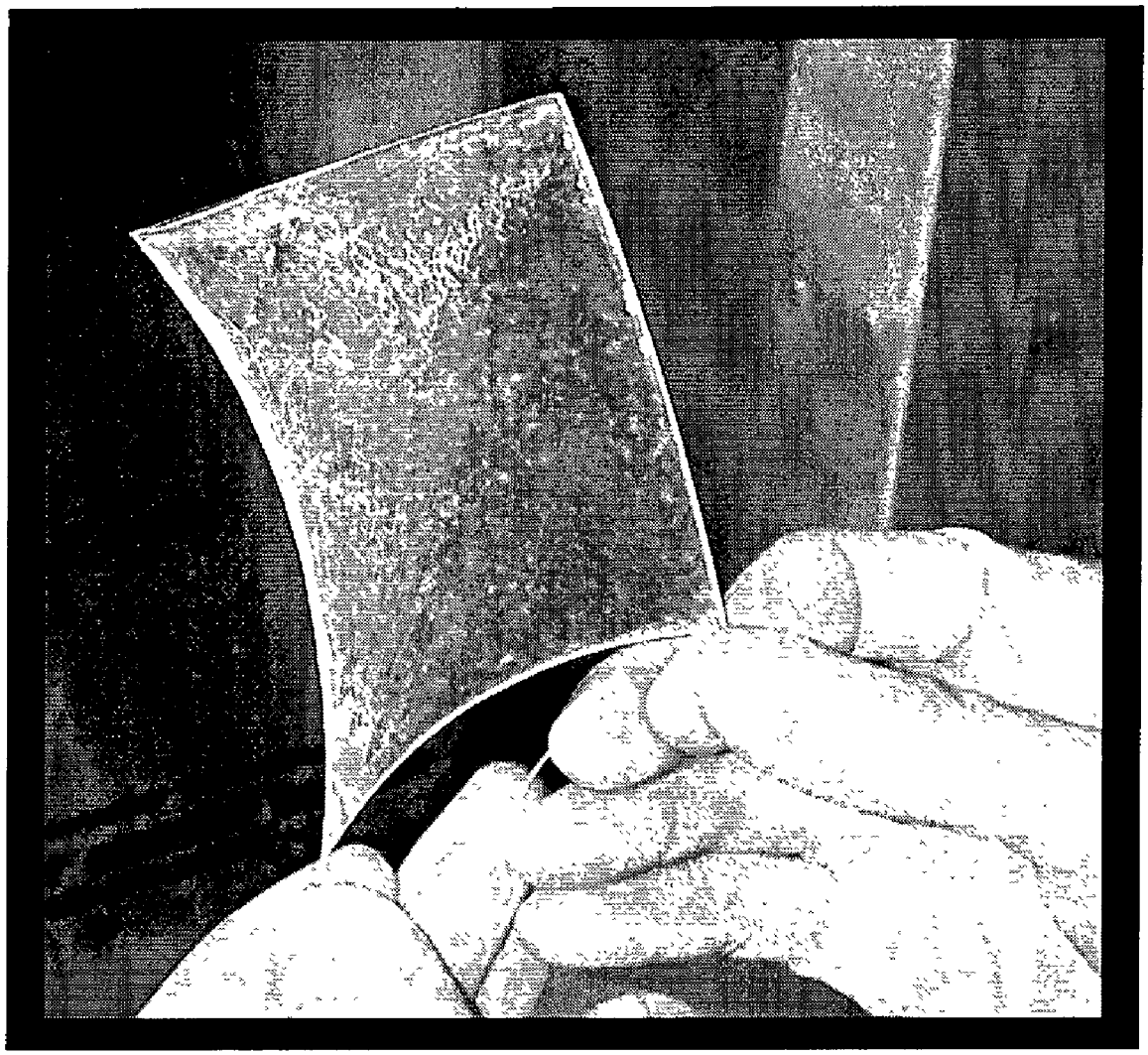
FIG. 1(b) is a photograph of a tissue sheet supported by two tissue control rods.
Figure 2:
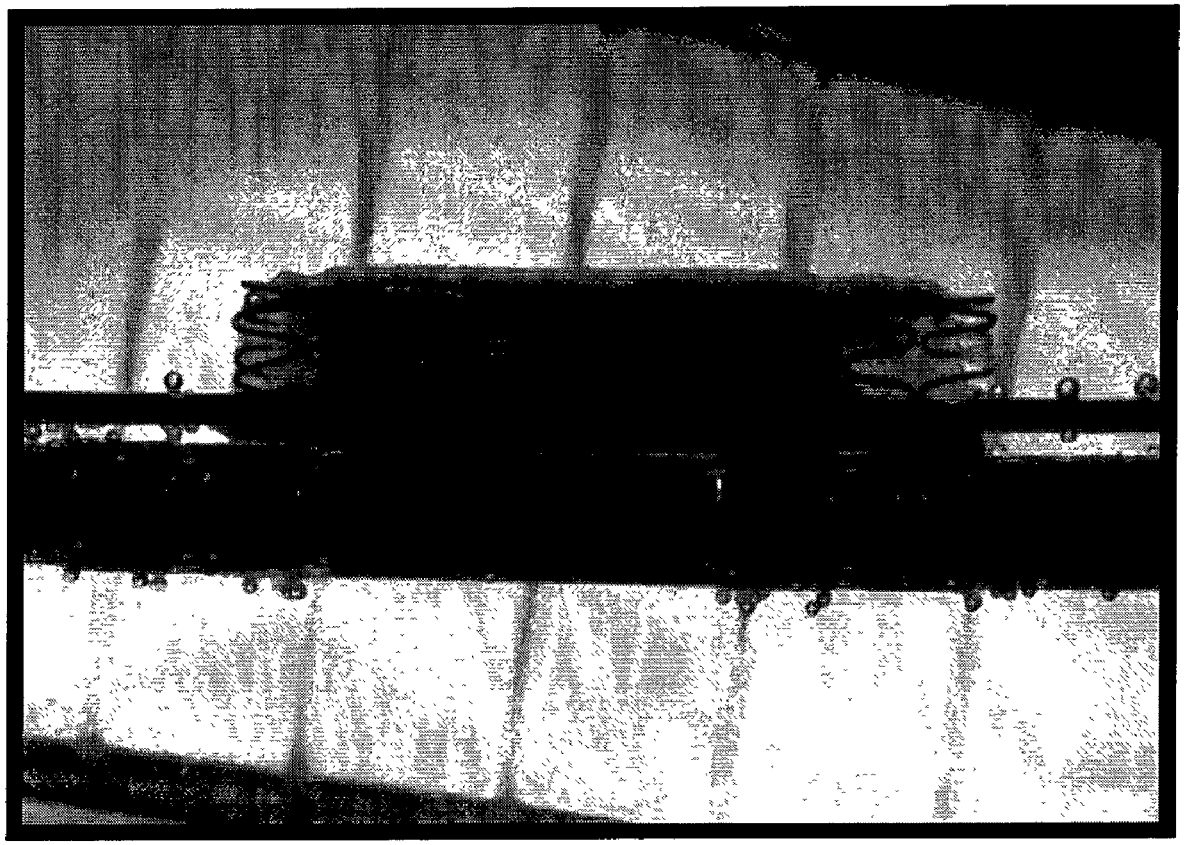
FIG. 2 is a tissue sheet-wrapped stent supported by a clamping system in a maturation bioreactor.
Figure 3:
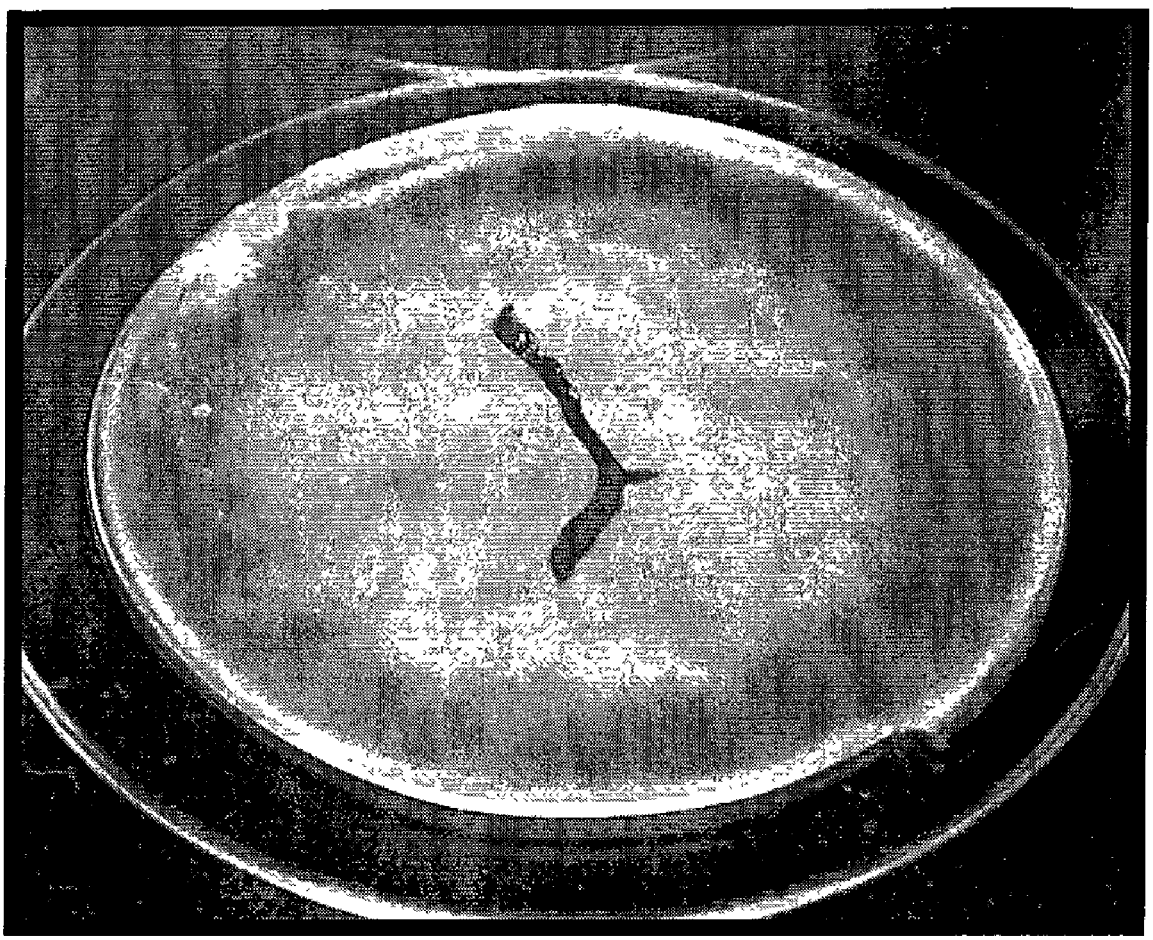
FIG. 3 is a tissue sheet supported by a ring control rod in a ciruclar 6-well plate.

A tissue manipulation device (e.g., control rods) are made from relatively inert biocompatible materials (including, but not limited to, Teflon®, magnetic material, a magnetizable material, a polypropylene, a steel (stainless steel) or a steel alloy, a titanium or a titanium alloy, a polystyrene, a glass, and any combination thereof). In another aspect, one or more tissue manipulation device(s)s are temporarily integrated into a robust tissue sheet during the growth and proliferation phase of cells in culture. During this phase, cells are seeded onto a cell growth substrate in a culture container and the cells grow and envelop a tissue manipulation device (e.g., one or more control rods). As the cells and their corresponding matrix proteins grow and are deposited, respectively, during maturation into a tissue sheet, the cells grow onto or adhere to and envelop a tissue manipulation device (e.g., one or more control rods). In order to assemble these sheets into a more complex three-dimensional tissue, the tissue manipulation device(s) can be used to detach the tissue sheet and support it during assembly and manipulation (FIG. 1). The control rods can also be used to magnetically secure or manipulate the sheets using external magnets and ferrous containing rods. For example, a ferrous tissue manipulation device coated with Teflon can be used to hold a tissue to a plate by magnets placed on the external surface of a culture container.

By "cell growth substrate" means any number of materials and compositions, many of which are currently commercially available, including for example, a tissue culture plate of a rectangular or circular shape having a growth area of about 1 cm$^2$ to greater than 500 cm$^2$, multiwell tissue culture plates having 2 wells to more than 90 wells per tissue culture plate, and tissue specimen slides as used in microscopic analysis. Other cell growth surfaces and devices are readily apparent to those of skill in the art. The methods and apparatus of the invention can be used with any of the foregoing cell or tissue culture plates, slides and devices.

A tissue sheet can be removed from culture utilizing a tissue manipulation device and can be further manipulated using the tissue manipulation device as needed to give rise to a desired organ or structure. Once the tissue sheet has been shaped into the appropriate organ or structure, the tissue manipulation device can be removed from the sheet. By making the tissue manipulation device from a non-adherent material or a material that cells bind to only weakly, such as stainless steel or ePTFE, the tissue manipulation device can be removed without damaging the tissue sheet. In other applications, it is conceivable that stronger adhesion would be desirable in which case different materials such as treated polystyrene is used. In yet other applications of the technology biodegradable materials may be desirable including, for example, polylactic acid, polyglycolic acid, collagen based material, cat gut sutures, and the like. Typically the tissue manipulation devices are substantially non-porous or non-porous thereby making it easier to remove the devices when needed.

Additionally, as discussed elsewhere herein, the integrated tissue manipulation device can also be used to increase/promote cell adhesion and/or the formation of a tissue sheet in a culture container. Accordingly, the invention provides methods to simplify the manipulation of films or membranes of living tissues as required in many tissue-engineering techniques and in the formation of tissue sheet-based vascular grafts and tissue sheet-wrapped stents. In general, the tissue manipulation devices (e.g., rods) are introduced into a cell culture such that they become integrated into a tissue or are in contact (e.g., not intergrated into the tissue) with the tissue comprising a population of cells as the cells proliferate. The tissue manipulation devices should be mechanically robust enough to support a tissue during normal handling, tissue manipulation and/or tissue engineering techniques, or test procedures.

Typically a tissue manipulation device will comprise a material that can be sterilized by conventional techniques such as heat, ethylene oxide, or gamma sterilization. The tissue manipulation device should be of a biocompatible material in order to prevent cytotoxic effects upon cells. Depending upon the desired culture conditions, tissue construct to be made, and cell types present, the tissue manipulation device may be made of either a biodegradable or a non-biodegradable material. For example, where the tissue construct comprises a three-dimensional structure that prevents easy removal of the tissue manipulation devices or removal of the tissue manipulation device would result in undesirable damage to a tissue sheet, then the tissue manipulation devices should be made of a biodegradable material.

In one particularly embodiment, at least two tissue manipulation devices (e.g., 2, 3, 4, . . . , or more than 10) comprising rods are made from 316 stainless steel wires approximately 0.050 inches in diameter. The rods are bent to the shape of the cell culture container, then steam sterilized. Cells are seeded in a culture container comprising the tissue manipulation devices and allowed to grow to a confluent monolayer or tissue sheet. The tissue manipulation rods are position and secured using magnets placed on the outside of a culture container (e.g., a flask) to act as clamps. The tissue manipulation rods are then left in place until such time as the cells of a tissue sheet substantially envelop the tissue manipulation devices. Cells of the tissue grow onto and envelop the stainless steel and only weakly adhere thereby integrating the tissue manipulation rods into the tissue sheet. When the tissue sheet reaches a desired mechanical characteristic, the tissue sheet and tissue manipulation device combination can be peeled away from the original cell culture substrate once the magnetic clamps are removed. The tissue manipulation devices can now be used to manipulate the tissue. For example, where a desired tissue construct comprises a vascular graft such as a blood vessel or tissue-wrapped stent, the tissue manipulation devices can be loaded onto a rotating mandrel such that the sheet can be fed into an automatic rolling device. Likewise, the sheets can be more easily and reproducible handled for the assembly of other tissue engineered organs like skin, livers, ligaments or heart valves where it is necessary to arrange sheets or segments of sheets into stacks.

The tissue manipulation device can be withdrawn from a cell sheet or tissue quite easily when the tissue manipulation device comprises a relatively inert material such as stainless steel, untreated Delrin™, or ePTFE. In some applications, it may be desirable to adhere the tissue manipulation devices to a cell sheet or tissue. For example, where a tissue will be used for mechanical testing it is not necessary to remove the tissue manipulation devices, so a wider range materials, including adherent materials can be used. In other aspects of the invention, where heart valves or temporary support livers (e.g., extracorporeal liver devices), the tissue manipulation devices may be a permanent fixture that also allows a wider range of materials to be used. Where biodegradable-biocompatible materials are used the materials should be robust enough in culture to help with the manipulation of the tissue sheet, but once manipulated and/or implanted would be resorbed by the cells or body. In another aspect, the tissue manipulation device may simply be cut away from the tissue sheet once it is no longer needed.

A number of cell types may be cultured on a cell growth substrate using standard cell culturing techniques. Typically the cells used in the methods and systems of the invention comprise adherent cell types. Such cells when cultured under appropriate conditions divide and expand to cover and adhere to a cell growth substrate. The cell types may be allogeneic or autologous with respect to a subject to which that a tissue construct derived from the cells is ultimately implanted or used.

Ideally, cells are harvested from an autologous source, expanded and manipulated in culture, then re-implanted into the donor (see, e.g., U.S. Pat. Nos. 5,512,475; 5,780,299; and 5,866,420, which are incorporated herein by reference in their entirety). However, current tissue engineering strategies use a common technique, which is to culture the cells within a synthetic scaffold that provide requisite mechanical strength. These scaffolds are typically based on either resorbable polymers or porous meshes of biological materials such as collagen foams.

The methods and systems provided herein do not require synthetic cell scaffolds and are based in part upon the pioneering work of Auger and L'Heureux U.S. Pat. No. 5,618,718 and L'Heureux and McAllister U.S. patent application Ser. No. 09/444,520, the disclosures of which are incorporated herein by reference.

As one beneficial aspect of the invention there is provided techniques to culture a subject's own cells into a robust sheet. The invention provides compositions and methods to generate sheets of autologous and/or allogenic cells. These cell sheets are robust and can be shaped or molded into a variety of organs, including blood vessels, heart valves, and the like. The cells in the sheet can be manipulated into a desired shape or structure prior to or during implantation to assist in the replacement of organs or to assist in the reconstruction and/or healing of an existing organ.

Additionally, the tissue manipulation device can act as a support structure for more complex three dimensional structures such as heart valves. Prior art describes various techniques to suture or glue xenogenic tissue such as bovine pericardium to a heart valve frame, however, these technologies do not describe a technique to produce an autologous heart valve formed by mounting a robust sheet of human cells as described herein onto a heart valve frame work. There are a variety of possibilities envisioned. In one embodiment, the autologous human sheet is grown directly onto the heart valve frame work such that the tissue adheres to the framework during the culture process. This would likely require a non-planar culture dish that would allow the formation of an annular ring with tissue that forms the valve leaflets. In a similar configuration, the sheet can be grown onto the tissue manipulation framework in a planar configuration and then folded into a three dimensional configuration suitable for use as a heart valve. In both cases, the tissue sheet can be grown as described herein, detached from the cell culture substrate, and then attached to the valve frame work by chemical or mechanical means as is known in the art. This includes, but is not limited to, sewing, suturing, gluing, hooking, clamping, riveting etc. In all configurations, this invention describes a technique to produce a novel heart valve where the leaflets of the valve are formed by an autologous tissue engineered sheet.

As discussed above a tissue sheet may comprise any number of various cell types. Stromal cells including, for example, fibroblasts may be derived from a number of organs including, for example, the skin, pancreas, liver, and the like. Samples from which the fibroblasts are derived include, for example, from a biopsy (where appropriate), from a cadaver, or from disposed organ tissue. The fibroblast may be derived from the same organ for which they will be ultimately used to develop a tissue-engineered organ in vitro (e.g., derived from cardiovascular tissue for development of a vascular graft). Typically the fibroblast will be obtained from the same individual and later reimplanted (i.e., autologously). Precursor cells (e.g., stem cells of a particular tissue) that are not fully differentiated or that lack a particular MHC may be used. Such cells have the advantage of not inducing an immune response due to recognition of a fully differentiated cell as being "non-self". There are a number of stem cells and precursor cells known in the art (e.g., mesenchymal stem cells, hematopoietic stem cells, circulating stem cells, endothelial stem cells, embryonic germ cells, and the like), which are applicable to the culturing techniques of the invention so long as the cells are adherent or differentiated to adherent cells during culturing.

Stromal cells (e.g., fibroblasts) may be obtained by treatment of an appropriate organ or tissue that is to serve as the source of the stromal cells. Techniques for treatment of an organ or tissue to obtain stromal cells are known to those skilled in the art (see, e.g., Freshney, Culture of Animal Cells. A Manual of Basic Technique, 2d Ed., A. R. Liss, Inc., New York, 1987, Ch. 9, pp. 107–126). For example, the tissue or organ can be mechanically disrupted and/or treated with digestive enzymes or chelating agents to weaken the interactions between cells making it possible to obtain a suspension of individual cells. Typically the method will include a combination of mechanical disruption, enzyme treatment and chelating agents. In one technique the tissue or organ is minced and treated simultaneously or subsequently with any of a number of digestive enzymes either alone or in combination. Examples of enzymes useful in dissociating cells include, but are not limited to, trypsin, chymotrypsin, collagenase, elastase, hyaluronidase, DNase, pronase, dispase, and the like. Mechanical disruption can also be accomplished by, for example, the use of blenders, sieves, homogenizers, pressure cells, and the like.

The resulting suspension of cells and cell clusters can be further divided into populations of substantially homogenous cell types. This can be accomplished using standard techniques for cell separation including, for example, positive selection methods (e.g., clonal expansion and selection of specific cell types), negative selection (e.g., lysis of unwanted cells), separation based upon specific gravity in a density solution, differential adherence properties of the cells in the mixed population, fluorescent activated cell sorting (FACS), and the like. Other methods of selection and separation are known in the art (see, e.g., Freshney, Culture of Animal Cells. A Manual of Basic Techniques, 2d Ed., A. R. Liss, Inc., New York, 1987, Ch. 11 and 12, pp. 137–168).

One specific method of isolating stromal cells (e.g., fibroblasts) includes the mincing of a tissue in Hank's Balanced Salt Solution (HBSS) or other similar solution. The tissue is then incubated in a solution of trypsin under conditions and for a time sufficient to separate the cells (e.g., at about 4° C. for 1 to 12 hours). The separated cells are typically suspended in a high protein medium (e.g., media with fetal bovine serum or human serum (including autologous serum)), pelleted by centrifugation and plated onto tissue culture plates. Fibroblasts, for example, typically attach to the tissue culture plastic before other cells, thereby giving rise to a population of fibroblast cells. The resulting population of fibroblasts cells are typically substantially homogenous, but may contain additional cell types including macrophages, endothelial cells, epithelial cells, and the like, present in the tissue from which the fibroblasts are isolated. The fibroblasts are then grown to confluence in the presence of a tissue manipulation device (e.g., a rod of biocompatible material), which facilitates growth of a robust sheet and/or removal of the confluent fibroblast culture (e.g., a tissue sheet of fibroblasts) and manipulation of the confluent tissue sheet of cells to develop a tissue construct.

A sheet grown from fibroblast or other cell types are grown for periods of days to weeks in a culture container. Typically the cell sheets are grown for about 1–24 weeks, depending on the application, donor age, viability of the particular cell population, and the like. A culture container includes any number of materials and compositions, many of which are currently commercially available, including for example, a tissue culture plate of a rectangular or circular shape having a growth area of about 1 $cm^2$ to greater than 500 $cm^2$, multiwell tissue culture plates having 2 wells to more than 90 wells per tissue culture plate, and tissue specimen slides as used in microscopic analysis. Other cell growth surfaces and devices are readily apparent to those of skill in the art. The methods and apparatus of the invention can be used with any of the foregoing cell or tissue culture plates, slides and devices.

In most cell culture applications, adherent cell cultures can only be maintained for a few days to a few weeks before the individual cells release from a substrate. The addition of agents that promote cell growth, viability and/or adhesion can be used during the culture process. For example, addition of agents such as ascorbic acid, retanoic acid, and copper can be used to increase the production of extracellular matrix proteins thereby generating a more robust tissue sheet of cells. Moreover, by treating the cell culture surface/substrate with extracellular matrix proteins or other factors (e.g., a protein such as gelatin or fibrin), adhesion can be prolonged. The introduction of one or more tissue manipulation device(s)s (e.g., a plurality of control rods), such as those described herein, can be used to hold down the edges of the sheet on a culture container or substrate thus preventing spontaneous sheet detachment. The rods or tissue manipulation device can be designed such that they generate significant clamping forces (e.g., via gravity, magnetic forces and the like) to effectively secure the sheet. Moreover, the rods can be made of a biocompatible material such as ePTFE (e.g., a ePTFE outer surface and a metallic core) or stainless steel that will be slightly adherent to the cells present in a tissue sheet. In this manner, once a tissue sheet is removed from the culture surface it can be handled easily. This is an important development for both design and manufacturing that has not been described previously.

In another aspect, a stent-less tubular construct can be made comprising cells grown to a robust tissue sheet. In this aspect of the invention, the tissue sheet is removed from culture and manipulated using one or more tissue manipulation device(s)s that have been integrated through cellular growth into the tissue sheet. The stent-less tubular construct is mechanically formed by creating a cylindrical structure comprising the tissue sheet. The cylindrical structure will comprise one or more layers or cells and/or one or more layers of the tissue sheet perpendicular to the radius of the cylindrical tubular structure.

In one aspect of forming the tubular structure the tissue sheet is manipulated around a tubular mold or mandrel and then the tubular mold or mandrel is removed. For example, once a tissue sheet of cells is obtained, it can be rolled on the outer surface of a tubular support (e.g., a mold) of varying diameter to give it a tubular form. If the sheet is held in place while rolled up for a few hours in suitable cell culture conditions, it will adhere to itself relatively firmly and will stay in its tubular form, around its tubular mold. Alternatively, the ends may be sewed or glued to one another to assist in the formation of a tubular structure. The tubular tissue hence created may be kept in culture conditions for extended periods of time and submitted to various culture conditions to influence its ongoing development (ascorbic acid, serum, mitogens, and the like). The tubular mold is typically made of a "non-sticky" material thereby not allowing adhesion between the cell sheet and the material in order to facilitate removal of the mold from the lumen of the tissue sheet. Examples of such "non-sticky" material include ePTFE, polystyrene, stainless steel, and the like. At the end of a maturation period, the tubular tissue can be slid off its tubular mold to provide the basic scaffold for the construction of a more complex tissue culture system. For example, endothelial cells can be seeded on the inner surface of a tubular tissue sheet and/or smooth muscle cells on the exterior surface, hence producing a basic blood vessel construct or prosthesis. Such a tubular tissue prosthesis can be useful in tissue transplantation as it can be made from the cells of the graft recipient, thus circumventing immunological rejection of the prosthesis. Furthermore, the tubular tissue can be rolled up in a similarly produced sheet to obtain a multi-layer tubular tissue sheet. Cells which form additional layers can be of identical nature to the cells of a first layer to obtain a thicker tissue, or of different origin (such as endothelial, smooth muscle cells, and the like).

In addition to fibroblasts, other cells may be added to tissue sheet either before or after removal from culture. Such additional cells comprise parenchymal cells such as smooth muscle cells and/or endothelial cells. Sprinkling the sheet with endothelial cells, for example, helps to grow vascular networks (vasovasorum) within the wall of the rolled vessel. In normal vascular tissue cell layers form creating distinct areas of a blood vessel. Endothelial cells are found in the highest number in the lumen of the blood vessel and smooth muscle cells present on the external surface of the blood vessel. Fibroblasts and other stromal cells are present between the endothelial and smooth muscle cells. Accordingly, the seeding of a tissue sheet can performed such that the endothelial, fibroblast and smooth muscle cell layers are present in the vascular graft. For example, fibroblasts may be cultured to form a robust tissue sheet of cells, the tissue sheet is then seeded with endothelial cells whereupon manipulation of the tissue sheet comprising the endothelial cells into a tubular structure results in the endothelial cells being present on the lumen surface of the tubular structure. Smooth muscle cells can then be seeded on the external surface of the tubular structure. The tissue sheet-based construct can then be implanted or further cultured for a time sufficient to allow the cells to interact and grow. Such culture conditions may include culturing the tubular construct in a bioreactor that generates flow and shear stresses typically present in a vascular tissue. A bioreactor similar to that described in U.S. Pat. No. 6,121,042 (the disclosure of which is incorporated herein by reference) may be used.

In another aspect of the invention, a tissue-wrapped stent can be generated. In this aspect, a tissue sheet is manipulated around (e.g., to surround one or more times) a biocompatible and/or biodegradable material (e.g., a stent) having a lumen, and the lumen is then seeded with endothelial cells and/or smooth muscle cells. Alternatively, endothelial cells and/or smooth muscle cells may be added to the biocompatible and/or biodegradable material prior to adding the fibroblast sheet. In one aspect of the invention a biocompatible stent is used as a support for forming the tubular structure. The biocompatible stent is mounted on a temporary support mandrel and the tissue sheet is then layered one or more times around the biocompatible stent. Cells including, for example, endothelial cells, pericytes, macrophages, monocytes, plasma cells, mast cells, adipocytes, and the like, may be added independently or together. The biocompatible and/or biodegradable material typically will be substantially non-porous (e.g., lacking interstitial spaces) and where such pores are present they are of a size that does not allow for diffusion of the cell types into/through the material. Examples of pores that are sufficiently small range in size from 10 μm to 100 μm. In one aspect, the biocompatible material is a "non-sticky" material thereby not allowing adhesion between the cell sheet and the material. Examples of such "non-sticky" material include ePTFE, polystyrene, stainless steel, and the like.

The sheet-wrapped stent has many advantages that distinguish it from other covered stents. These include: (a) the stent can be coated with a subject's own cells (e.g., fibroblasts, endothelial cells, and/or smooth muscle cells) which will slow the foreign body response and subsequent failures; (b) where the subject's cells are genetically modified, such cells and their progeny will continue to produce a therapeutic and/or diagnostic agent (e.g., a polypeptide or polynucleotide); (c) a tissue engineered vascular graft comprising a sheet of cells, unlike simple cell seeded stents, provides a barrier to migrating cells and subsequent intimal hyperplasia; (d) the sheet can be seeded with functional endothelial cells, thus providing a uniform lumen with an anti-thrombogenic surface; and (e) a sheet of cells can be assembled into a tubular construct that can act as a stand alone stent or a stand alone bypass conduit.

In one aspect, the invention provides a process by which a stent is wrapped in a sheet of autologous or allogenic cells to provide a tissue-wrapped stent. A stent refers to any device capable of being placed into contact with a portion of a wall of a lumen of an artery, vessel, or other tubular organ structure. Stents useful in the methods and compositions of the invention include classical stents used in intravascular applications, as well as any prosthesis that may be inserted and held where desired in a lumen.

Typically, a stent has a lumen wall-contacting surface and a lumen-exposed surface. A stent is shaped generally as a tubular structure but includes discontinuous tube structures. A lumen-wall contacting surface is the outside surface of the stent and the lumen-exposed surface is the inner surface of the stent. The stent can include polymeric elements, metallic elements, filamentary elements, or combinations thereof. In one aspect the surfaces (e.g., the lumen-wall contacting surface and/or the lumen exposed surface is coated with extracellular matrix material (e.g., fibronectin, fibrin, collagen, or other extracellular matrix material) prior to contact with a tissue sheet in order to promote adherence of the tissue sheet to the stent.

In one aspect a deformable metal wire stent is used in conjunction with the tissue sheet. An example of a metal wire stent is described in U.S. Pat. No. 4,886,062. Other metallic stents useful in this invention include those described in U.S. Pat. No. 4,733,655 and U.S. Pat. No. 4,800,882. Polymeric stents can also be used in this invention and include stents comprising biodegradable and non-biodegradable materials.

Stents useful in the invention generally comprise a biocompatible material. In some aspect the stent is coated with a drug that assists in reducing restenosis or for the delivery of a therapeutic agent. Such drug-eluting stents are also useful in the methods and compositions of the invention in combination with both genetically engineered tissue sheets as well as tissue sheets comprising cells that have not been genetically engineered. Generally stent designs include those described in U.S. Pat. Nos. 4,733,655, 4,800,882, and 4,886,062. Such designs include both metal and polymeric stents, as well as self-expanding and balloon-expandable stents. Examples of drug-eluting stents include those described in U.S. Pat. No. 5,102,417 and in International Patent Application Nos. WO 91/12779 and WO 90/13332, (the disclosures of which are incorporated herein).

In one aspect, the invention provides a cell-based sheet wrapped stent technology. As one beneficial aspect there is provided techniques to culture a subject's own cells into a robust sheet. These robust sheets of cells can then be applied to stents. Once a sheet of cells is obtained, it can be rolled on the outer surface of a tubular support of varying diameter to give it a tubular form. If the sheet is held in place while rolled up for a few hours in suitable cell culture conditions, it will adhere to itself relatively firmly and will stay in its tubular form, around its tubular support. The tubular tissue hence created may be kept in culture conditions for extended periods of time and submitted to various culture conditions to influence its ongoing development (ascorbic acid, serum, mitogens, and the like).

In one aspect the tubular support may comprise an anti-thrombotic and/or anti-restenosis agents including proteins, polypeptide, peptides, peptidomimetics, and small molecules. One particular advantage is that the robust sheet of cells slowly replaces that stent material as the anti-thrombotic agents degrade or are used up. By this technique the subject's own cells are allowed to replace and/or reconstruct the damaged vasculature. Anticoagulant substances such as heparin and thrombolytic agents have also been incorporated into a stent, as disclosed, for example, in U.S. Pat. Nos. 5,419,760 and 5,429,634.

A particular advantage of the tissue wrapped-stents of the invention compared to a seeded cell stent is that the robust tissue sheet of cells provides an immediate barrier that prevents infiltration of extraluminal cells. In contrast, cell seeded stents do not provide the same barrier function and thus extraluminal cells are capable of infiltrating the stent and the lumen of the sent thereby leading to intimal hyperplasia. In order to promote the barrier function of the sheet-wrapped stents, the tissue sheet may be cultured for a time sufficient and under sufficient conditions to allow fusion between the cells of the tissue sheet and/or the stent. In some aspects, the sheet would have a shorter maturation time after wrapping onto the stent so that the stent can be expanded within the sheet while the sheet simply unwinds slightly. In another aspect, the stent material is biodegradable or may be entirely absent. During the culture time, the tissue construct can be seeded with additional cell types (e.g., endothelial cells and/or smooth muscle cells) either autologous or allogeneic. The addition of such additional cell types can assist to reduce the likelihood of thrombosis.

In one aspect, the invention provides a cell-based sheet wrapped stent technology. As one beneficial aspect there is provided techniques to culture a subject's own cells into a robust sheet. These robust sheets of cells can then be applied to stents. Once a sheet of cells is obtained, it can be rolled on the outer surface of a tubular support of varying diameter to give it a tubular form. If the sheet is held in place while rolled up for a few hours in suitable cell culture conditions, it will adhere to itself relatively firmly and will stay in its tubular form, around its tubular support. The tubular tissue hence created may be kept in culture conditions for extended periods of time and submitted to various culture conditions to influence its ongoing development (ascorbic acid, serum, mitogens, etc.).

In one aspect the tubular support may comprise an anti-thrombotic and/or anti-restenosis agents including proteins, polypeptide, peptides, peptidomimetics, and small molecules. One particular advantage is that the robust sheet of cells slowly replaces that stent material as the anti-thrombotic agents degrade or are used up. By this technique the subject's own cells are allowed to replace and/or reconstruct the damaged vasculature.

In yet another aspect of the invention there is provided an expandable stent that is covered by a tissue sheet of autologous and/or allogenic fibroblasts to form a tissue construct. In one aspect, the fibroblasts are derived from fibroblast precursor cells (e.g., mesenchymal stem cells, hematopoietic stem cells, circulating stem cells, and the like) and thus typically lack the antigenic determinants that would be indicative of a cell derived from a particular individual. The fibroblasts or precursor cells may be genetically modified to express or over express polypeptides or polynucleotides that prevent or retard restenosis, thrombosis, and/or reduce inflammation. Such a tissue construct may include the seeding of autologous endothelial cells within the lumen of the stent to reduce thrombosis.

In another aspect of the invention, the cells of a tissue sheet can be genetically modified to express diagnostic and/or therapeutic product (e.g., a polypeptide or polynucleotide) to assist in tissue healing, replacement, maintenance, diagnosis, and the like of an implanted tissue sheet. Unlike the drug eluting coatings, however, these cells, and their progeny, can be engineered to continually produce a desired gene product. In another aspect the cells may only transiently produce a product. Methods of permanent and transient transfections are known and will be described further herein. One particular advantage of utilizing a tissue sheet comprising genetically engineered cells is that a large amount of cells may be utilized compared to simply seeding a relatively few number of genetically engineered cells.

The cells present in a tissue sheet may be genetically modified to produce a diagnostic or therapeutic product. By diagnostic product is meant a product that is expressed due to a genetic transformation of the genotype of a cell wherein the product assists in the diagnosis of, for example, proper stent or tubular tissue placement or the failure of a stent or tubular tissue. A diagnostic product can be a polypeptide, peptide, polynucleotide, or a by-product of a reaction resulting from expression of a product comprising an enzyme. For example, as shear stress increases in an implanted stent due to intimal hyperplasia, specific promoters can be activated to express a marker indicative of stent failure. By a therapeutic product is meant a product that is expressed due to a genetic transformation of the genotype of a cell wherein the product assists in the treatment and/or patentcy of a stent or tubular tissue. The therapeutic product may be a polypeptide, peptide, peptidomimetic, soluble ligands (e.g., homooligomers, heterooligomers), and/or polynucleotides (e.g., antisense or ribozyme molecules). Examples of therapeutic products include anti-inflammatory factors such as anti-GM-CSF, anti-TNF, anti-IL-1, anti-IL-2, and the like. Alternatively, the cells in the tissue sheet may be genetically modified to inhibit expression of polypeptide or polynucleotide that promotes inflammation, e.g., GM-CSF, TNF, IL-1, IL-2, or inhibit expression of MHC in order to lower the risk of tissue rejection. As yet another aspect, the cells of the tissue sheet can be genetically modified to block expression of a polypeptide or polynucleotide (e.g., a ribozyme or antisense molecule) that causes smooth muscle cells to proliferate and migrate into the lumen of a stent of a vascular graft to prevent neointimal hyperplasia.

A polynucleotide or nucleic acid molecule refers to a polymeric form of nucleotides at least 9 bases in length. An isolated polynucleotide is a polynucleotide that is not immediately contiguous with either of the coding sequences with which it is immediately contiguous (one on the 5' end and one on the 3' end) in the naturally occurring genome of the organism from which it is derived. The term therefore includes, for example, a recombinant DNA or RNA that is incorporated into a vector, a viral vector, or into the genome of a host cell such that the isolated polynucleotide is heterologous to the genome or location in the genome of a host cell. The nucleotides present in a polynucleotide used for transformation and/or transfection of a host cell can be ribonucleotides, deoxyribonucleotides, or modified forms of either nucleotide. The term includes single- and double-stranded forms of nucleic acid molecules.

A polynucleotide may be any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, polynucleotide as used herein can also refer to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. As discussed more fully below such modified polynucleotides may be coated on biocompatible stents where the polynucleotides are taken up by cells that come into contact with the stent (see, e.g., U.S. Pat. No. 5,962,427, which is incorporated herein in its entirety).

Cells present in a tissue sheet may be genetically engineered using recombinant DNA techniques to generate a recombinant host cell transformed or transfected with a polynucleotide that encodes a product of interest (e.g., a polypeptide or polynucleotide that provides a diagnostic and/or therapeutic benefit). Methods of transforming or transfecting cells with exogenous polynucleotide such as a DNA molecule are well known in the art and include techniques such as calcium-phosphate- or DEAE-dextran-mediated transfection, protoplast fusion, electroporation, liposome mediated transfection, direct microinjection and adenovirus infection (Sambrook, Fritsch and Maniatis, 1989).

The most widely used method is transfection mediated by either calcium phosphate or DEAE-dextran. Depending on the cell type, up to 90% of a population of cultured cells can be transfected at any one time. Because of its high efficiency, transfection mediated by calcium phosphate or DEAE-dextran is the method of choice for experiments that require transient expression of the foreign DNA in large numbers of cells. Calcium phosphate-mediated transfection is also used to establish cell lines that integrate copies of the foreign DNA, which are usually arranged in head-to-tail tandem arrays into the host cell genome.

Yet another method of transfection or transformation that can be used to generate genetically engineered/genetically-modified cells includes the technique of electroporation. The application of brief, high-voltage electric pulses to a variety of mammalian cells leads to the formation of nanometer-sized pores in the plasma membrane of the cell(s). DNA is taken directly into the cell cytoplasm either through these pores or as a consequence of the redistribution of membrane components that accompanies closure of the pores. Electroporation can be extremely efficient and can be used both for transient expression of cloned heterologous polynucleotides and for establishment of cell lines that carry integrated copies of a polynucleotide. Electroporation, in contrast to calcium phosphate-mediated transfection and protoplast fusion, frequently gives rise to cell lines that carry one, or at most a few, integrated copies of a heterologous polynucleotide.

Other methods that can be used include liposome transfection, which involves encapsulation of DNA and RNA within liposomes, followed by fusion of the liposomes with the cell membrane. Direct microinjection of a polynucleotide into nuclei has the advantage of not exposing the polynucleotide to cellular compartments such as low-pH endosomes. Microinjection is also used as a method to establish lines of cells that carry integrated copies of a polynucleotide of interest.

The use of retroviral vectors and adenoviral vectors for cell transfection is known in the art. Adenovirus vector-mediated cell transfection has been reported for various cells (Stratford-Perricaudet, et al. 1992). A host cell of the invention is typically a eukaryotic stromal or parenchymal cell that can be grown in culture to form a robust tissue sheet. The host cell(s) may be autologous to the subject ultimately intended to receive the host cell(s) or may be allogeneic.

It should be noted that a polynucleotide used to transform or transfect a host cell need not encode a product. A polynucleotide useful in the invention can be a promoter or enhancer element that is flanked by oligonucleotide sequences that are identical to regions in the host cell genome. Upon introduction of the promoter or enhancer construct the oligonucleotides align with the host cell genome and the promoter or enhance sequence is thereby integrated into the host cell genome during normal cellular replication. Typically the promoter or enhancer element will be heterologous to the location of integration and results in the modified expression (e.g., the up regulation or down regulation) of a gene sequence in the host cell genome. Where down regulation occurs the heterologous sequence disrupts normal expression of a gene. Examples of promoter/enhancer elements useful in the genetically engineered tissue-wrapped stents and tissue sheet-based vascular grafts include an elastin or elastase I regulatory element. The deposition of elastin is correlated with specific physiological and developmental events in different tissues, including the vascular grafts. For example, in developing arteries, elastin deposition appears to be coordinated with changes in arterial pressure and mechanical activity. The transduction mechanisms that link mechanical activity to elastin expression involve cell-surface receptors. Once elastin-synthesizing cells are attached to elastin through cell-surface receptors, the synthesis of additional elastin and other matrix proteins may be influenced by exposure to stress or mechanical forces in the tissue.

In general, plasmid vectors containing replicon and control sequences which are derived from species compatible with the host cell are used to genetically modify a host cell. The vector ordinarily carries a replication site, as well as marking sequences which are capable of providing phenotypic selection in transformed cells. In constructing suitable expression plasmids, the termination sequences associated with heterologous polynucleotides are also introduced into the expression vector downstream from the sequences to be expressed to provide polyadenylation of the mRNA and termination.

For example, expression vectors for use in transforming or transfecting cells ordinarily include an origin of replication, a promoter located upstream of the polynucleotide encoding a particular product to be expressed, along with any necessary ribosome binding sites, RNA splice sites, polyadenylation site, and transcriptional terminator sequences.

For use in mammalian cells, the control functions of the expression vectors are often derived from viral material. For example, commonly used promoters are derived from polyoma, Adenovirus 2, Cytomegalovirus and most frequently Simian Virus 40 (SV40). The early and late promoters of SV40 virus are particularly useful because both are obtained easily from the virus as a fragment which also contains the SV40 viral origin of replication. Smaller or larger SV40 fragments can also be used, provided there is included the approximately 250 bp sequence extending from the HindIII site toward the BglI site located in the viral origin of replication. Further, it is also possible, and often desirable, to utilize promoter or control elements normally associated with the desired polynucleotide encoding the product to be expressed, provided such control sequences are compatible with the host cell systems.

An origin of replication can be provided by construction of the vector to include an exogenous origin, such as can be derived from SV40 or other viral (e.g., Polyoma, Adeno, VSV, BPV, CMV, rapalogue) source, or can be provided by the host cell chromosomal replication mechanism. If the vector is integrated into the host cell chromosome, the latter is often sufficient.

The genetically engineered tissue-wrapped stents and tissue sheet-based vascular grafts of the invention provide a method for introducing therapeutic products not only locally (e.g., to prevent intimal hyperplasia and restenosis) but also systemically to treat disease and disorders in a subject. In one aspect, the invention provides a suitable means for providing delivery of a therapeutic or diagnostic product and/or gene therapy. The usefulness of the genetically engineered tissue-wrapped stents and tissue sheet-based vascular grafts arises in part from the tissue which the genetically engineered tissue-wrapped stents and tissue sheet-based vascular grafts replaces. For example, intravascular drugs are administered to the blood stream often by repeated puncturing of the skin and veins with a needle in order to obtain a rapid systemic delivery of the drug or agent. The ability of the genetically engineered tissue-wrapped stents and tissue sheet-based vascular grafts to directly deliver a therapeutic agent to the blood stream avoids the often painful and infectious routes of administration using needles while at the same time maintaining a rapid systemic delivery of the agent. For example, the genetically engineered tissue-wrapped stents and tissue sheet-based vascular grafts comprising stromal cells can be genetically engineered to express anticoagulation products to reduce the risk of thromboembolism or to express anti-inflammatory gene products to reduce the risk of failure due to inflammatory reactions. For example, the cells of the tissue sheet can be genetically modified to express TPA, streptokinase or urokinase to reduce the risk of clotting.

In another aspect, the cells of the tissue-wrapped stents and tissue sheet-based vascular grafts can be genetically modified to express soluble receptors in the form of oligomers. A number of therapeutic oligomers are currently marketed for treatment of a variety of diseases and disorders. For example, soluble TNF-receptor oligomers sold under the trade name ENBREL® are used to treat a number of disease and disorders including rheumatoid arthritis, psoriatic arthritis, and the like. ENBREL is currently delivered by injection. The invention provides the ability to deliver ENBREL through genetically engineered tissue-wrapped stents and tissue sheet-based vascular grafts to treat, for example, arthritis, psoriasis and the like. Products delivered through genetically engineered tissue-wrapped stents and tissue sheet-based vascular grafts can be used to treat, for example: thrombus formation, inflammatory reactions, and fibrosis and calcification of the valves.

The cells present in the tissue sheet can be engineered to express such therapeutic products transiently and/or under inducible control, or as a chimeric fusion protein anchored to the cells of the tissue sheet. This expression can be triggered by mechanical signals such as fluid shear stress or stretch, or pharmacological agents. Another example is an anchored molecule comprising the ligand binding domain of a receptor (e.g., TNF-R), wherein the anchor is provided through an intracellular and/or transmembrane domain of a receptor or receptor-like molecule, fused to the ligand binding domain of a receptor. In another embodiment, the genetically engineered tissue-wrapped stents and tissue sheet-based vascular grafts can be used to provide a subject with a polypeptide or polynucleotide product for which the subject is deficient. In yet another aspect, the genetically engineered tissue-wrapped stents and tissue sheet-based vascular grafts are engineered to provide a product that is carried by the blood; e.g., cerebredase, adenosine deaminase, and an antitrypsin.

Cells used to develop a tissue sheet can be engineered using a recombinant DNA technology to transform or transfect a host cell (i.e., a cell that will be used to develop a tissue sheet) with a heterologous polynucleotide, which is then clonally expanded into a robust tissue sheet. The robust tissue sheet, which expresses a product from the heterologous polynucleotide, is then implanted into a subject who is deficient for that product. In another aspect, the tubular structures derived from the tissue sheets of the invention can be used to deliver therapeutic agents to not only the blood, but other tissues including other tubular tissue such as the genitourinary tract and gastrointestinal tract.

The use of the robust tissue sheet in delivery of a therapeutic product or through gene therapy has a number of advantages. First, since the culture comprises eukaryotic cells, the recombinant product will be properly expressed and processed to form an active product. Secondly, delivery and/or gene therapy techniques are useful only if the number of transfected cells can be substantially enhanced to be of clinical value, relevance, and utility; the robust tissue sheets of the invention allow for expansion and amplification (via cell division) of transfected cells into a robust tissue sheet that is ultimately implanted into a subject.

An advantage of the genetically modified cell sheets described herein is that the release of diagnostic and/or therapeutic agents can be dynamically controlled by triggering the cellular production by either pharmacological or physical means. For example, a polynucleotide encoding a product of interest (e.g., a polypeptide, antisense or ribozyme molecule) can be induced to express the product under a desired physical condition (e.g., shear stress) that induces, for example, tissue specific regulatory elements (e.g., elastin or elastase I regulatory elements). For example, a polynucleotide can be induced to express a therapeutic product as an intimal hyperplasia processes start to narrow the lumen of the stent or vascular graft due to increasing fluid shear stresses by engineering an elastin or elastase I regulatory element in operable association with a gene encoding a desired therapeutic or diagnostic product. In one aspect, the polynucleotide would produce an anti-restenotic agent or other therapeutic agent. In another aspect, the polynucleotide would produce a reporter molecule that would signal that the stent or vascular graft is loosing elasticity or viability thereby signaling that it should be replaced. Where the polynucleotide produces an anti-restenotic agent or other therapeutic agent a self-correcting dynamic balance is achieved without unnecessarily eluting the therapeutic agents (which may have systemic as well as local effects) at all times.

The tissue sheet-based constructs (e.g., the genetically engineered vascular grafts and tissue-wrapped stents) can be implanted in vivo or used for in vitro study of biological activities in response to various agents. Implantation in vivo of a vascular graft derived from a tissue sheet or a tissue-wrapped stent will typically be performed using stenting and/or angioplasty procedures.

In one embodiment, the construct is delivered via catheter by piercing through the wall of the healthy vessel near the proximal end of a diseased area of the vessel and bypassing the diseased area by then re-entering on the distal end of the diseased area. A percutaneous bypass would not be possible with current technologies, since normal stents do not have a membrane that would allow blood to pass through without leaking (i.e., typically stents are highly porous). Moreover synthetic grafts made from collagen or polymers or other synthetic scaffolds lack one or more of the 3 critical components of the tissue engineered stent or vessel: (1) endothelial cells; (2) adequate compliance; and/or (3) adequate mechanical strength. In another embodiment, the stent is delivered on a balloon catheter and then expanded in place. In another, the stent or rolled vessel is inserted through a small atherectomy (open artery) procedure. In yet another embodiment, the stent or rolled vessel is delivered in a fashion similar to classic bypass, where the ends of the graft are sewn into place. One advantage to this final embodiment is that sutures or other anchoring anastomotic devices can be pre-loaded onto the tissue engineered construct to facilitate insertion.

The invention described herein is formed by anchoring immature tissue to a cell culture substrate to allow prolonged maturation, which increases mechanical strength. Once the sheet is formed, it is a mechanical building block that can be used either with or without other mechanical devices (such as stents) in order to provide better treatment of cardiovascular disease via catheter based intervention.

The invention provides, a tissue-coated stent assembled using sheet-based tissue engineering techniques. In this embodiment, a robust sheet of autologous or allogenic fibroblasts is produced from cells seeded onto a culture flask. The sheet is assembled without the need for any exogenous matrix or scaffold. The sheet is formed by adding agents to the cell culture media that promote extracellular matrix production and/or adhesion such that the cell layer matures into a thick sheet that can be manipulated. Examples of agents that promote production of collagen include ascorbic acid, copper, and retanoic acid. Prolonged periods of culture increases production of extracellular matrix proteins, which provide the structural strength of the sheet. In order to prolong culture, the sheet can be anchored to the substrate using coatings on the substrate such as fibrin or gelatin or by clamping the sheet with magnet clamps or control rods. The sheet can also be anchored by growing it on a porous membrane that can later be detached and discarded.

The sheet is removed from the substrate and wrapped around a collapsed stent. The sheet-wrapped stent is matured for a period of time such that the cells of the sheet migrate onto the stent and envelope the struts of the stent. During this brief maturation (approximately 0–4 weeks) the stent becomes an integral part of the tissue in the sheet. During this time, autologous endothelial cells can be seeded to the inside of the stent to make an endothelialized lumen. If the sheet is wound about the stent several revolutions, it is important to arrest the maturation process prior to the individual plies of the sheet fusing strongly together. This is important, since, when the stent is deployed in the body, it must be expanded by a factor of 2 or 3 times its original diameter. Unless provisions are made such that the sheet has extraordinary elasticity (by overexpressing elastin production in the extracellular matrix, for example), the sheet will rupture during the expansion if it is well fused. If the sheet is only partially fused, however, the plies of the sheet will slip relative to each other slightly, thus allowing the diameter to increase without rupture of the tissue. The sheet-wrapped stent is delivered to the diseased artery via a catheter using techniques well known in the art. The stent is expanded using a balloon, and the catheter is withdrawn. The stent, embedded in the cellular sheet, is left behind. Blood clotting is reduced by the fact that the lumen of the sheet-wrapped stent is endothelialized. Migration of cells such as smooth muscle cells that cause failures by intimal hyperplasia is reduced by the presence of the sheet, which acts as a barrier. The foreign body responses to the stent are likewise attenuated since the stent is embedded in autologous tissue. This technique has been utilized in canine models and patentcy through 3 months was demonstrated.

In another embodiment, the cells that form the sheet can be genetically modified to over-express therapeutic agents that reduce the likelihood of failure by thrombosis or intimal hyperplasia. Similarly, the sheets can be transfected to overexpress agents that will change the composition of the extracellular matrix. Elastin, for example, can be overexpressed to increase the elasticity of the vessel and thereby reduce the likelihood of failures due to compliance mismatch at the anastomotic site.

In another embodiment, the stent can be manufactured from a resorbable material such that the sheet acts as a new lining for the diseased blood vessel. In this embodiment, the stent is used only as a delivery vehicle and a temporary mechanical support. The cells in this embodiment can also be transfected to reduce restenosis.

In another similar embodiment, the stent can be removed entirely. Since the tissue engineered construct is quite robust, it is possible to support the artery in the location of the ruptured plaque using the cylindrical roll of the cell-based sheet without any sort of stent. In this case, the sheet-based cylinder is formed by rolling the sheet around a temporary steel mandrel (a temporary stent), and then allowing a prolonged maturation phase. During this maturation phase, the plies of the sheet are allowed to fuse more completely in order to provide a more robust support. Since the tissue is not delivered on an expandable stent, it can be collapsed around the delivery catheter without the need for dramatic increases in diameter (in other words, the collapsed cylinder simply unfolds as it is inflated to its normal diameter by the balloon catheter).

In another embodiment, the sheet wrapped stent, can provide a basis for percutaneous bypass. That is, the sheet wrapped stent can be used to reroute blood flow around a blocked vessel rather than disrupting the plaque and flowing through the diseased artery. In this embodiment, the sheet-wrapped stent must be equipped with a device on the ends of the vessel that facilitates an anastomosis. This device seals the hole that must be made in order to make the native artery communicate with the bypass vessel. The percutaneous bypass is achieved by advancing the sheet wrapped stent to a point just proximal to the blockage, and then directing the delivery catheter through the wall of the diseased artery. The proximal end is then sealed using an anastomotic device as is known in the art. The sheet wrapped stent is advanced around the diseased artery, and is then reintroduced into the artery downstream of the blockage. Like the proximal end, the distal end must be sealed using an automatic anastomotic device. Ordinarily, passing the catheter through the wall of the native artery is to be avoided at all times. What makes this embodiment possible is that the stent is wrapped in a tissue that makes the bypass vessel relatively leak proof. When the native artery is pierced above and below the blockage, blood flow is re-routed around the blockage and through the wrapped stent. Similarly, the stentless embodiment of a cylindrically formed sheet as above can be used for this percutaneous bypass. That is, a sheet can be formed around a mandrel, matured so that the plies are well fused, and then modified such that an anastomotic device is included on each end. The entire construct is delivered percutaneously, and blood is re-routed around the blocked artery in the vessel formed from the sheet of cells. In both of these embodiments, the device can be further improved by genetically modifying the cells as described above.

A number of embodiments of the invention have been described. Nevertheless, it will be understood that various modifications may be made without departing from the spirit and scope of the invention.

What is claimed is:

1. A tissue culture method, comprising;
culturing a population of adherent cells in a tissue culture container in the presence of one or more tissue control rod(s), under conditions that allow the formation of a tissue sheet comprised of living cells and extracellular matrix formed by the cells, whereby the tissue sheet is in contact with the one or more tissue control rod(s); and
removing the tissue sheet from the culture container
wherein the one or more tissue control rod(s) anchors the tissue sheet therefore preventing unintentional detachment of the tissue sheet from the culture container.

2. The method of claim 1, wherein the tissue sheet is removed from the culture container using the one or more tissue control rod(s).

3. The method of claim 1, wherein the one or more tissue control rod(s) are a biocompatible material.

4. The method of claim 1, wherein the one or more tissue control rod(s) are substantially non-porous.

5. The method of claim 1, wherein the one or more tissue control rod(s) are comprised of a non-adherent material.

6. The method of claim 1, wherein the one or more tissue control rod(s) are comprised of a biodegradable material.

7. The method of claim 6, wherein the biodegradable material is selected from the group consisting of cotton, polylactic acid, polyglycolic acid, a blend of polylactic and polyglycolic acid, cat gut sutures, cellulose, gelatin, dextran, and any combination thereof.

8. The method of claim 1, wherein the one or more tissue control rod(s) are comprised of a non-biodegradable material.

9. The method of claim 8, wherein the non-biodegradable material is selected from the group consisting of a magnetic material, a magnetizable material, a polypropylene, a TEFLON, a steel or a steel alloy, a titanium or a titanium alloy, a polystyrene, a glass, and any combination thereof.

10. The method of claim 1, wherein the one or more tissue control rod(s) form a heart valve framework.

11. The method of claim 1, wherein the tissue sheet has a planar shape that can be folded or bent into a configuration by folding or bending the one or more tissue control rod(s).

12. The method of claim 1, wherein the culture container is selected from the group consisting of a tissue culture plate, a tissue culture dish, a tissue culture flask, and a roller bottle or other non-planar containers.

13. The method of claim 12, wherein the culture container comprises polystyrene.

14. The method of claim 12, wherein the culture container is electrostatically treated to promote adhesion of cells.

15. The method of claim 12, wherein the culture container is treated with an agent selected from the group consisting of fibrin, gelatin, fibronectin, vitronectin, RDG-peptide, collagens and antibodies and any combination therof.

16. The method of claim 1, wherein the population of cells is isolated from a human biopsy.

17. The method of claim 1, wherein the population of adherent cells are substantially homogenous.

18. The method of claim 1, wherein the population of adherent cells are selected from the group consisting of fibroblasts, fibroblast precursors, endothelial cells, mesothelial cells, smooth muscle cells, mesenchymal stem cell, hematopoietic stem cells, circulating stem cells, and any combination thereof.

19. The method of claim 1, further comprising substantially immobilizing the one or more tissue control rod(s) using a magnetic field.

20. The method of claim 1, further comprising using the one or more tissue control rod(s) for manipulating and/or shaping the tissue sheet into a desired tissue structure.

21. The method of claim 20, wherein the desired tissue structure is selected from the group consisting of a tubular construct, a stack of tissue sheets, a heart valve and a three dimensional tissue or organ.

22. The method of claim 1, wherein the one or more tissue control rod(s) is circular.

23. The method of claim 1, wherein the one or more tissue control rod(s) is bent to the shape of the cell culture container.

24. The method of claim 20, wherein the one or more tissue control rod(s) remains in the tissue structure.

* * * * *